United States Patent [19]

Ishiguro

[11] Patent Number: 4,530,751
[45] Date of Patent: Jul. 23, 1985

[54] ELECTROCHEMICAL CELL AND METHOD OF PRODUCING THE SAME

[75] Inventor: Fujio Ishiguro, Nagoya, Japan

[73] Assignee: NGK Insulators, Ltd., Japan

[21] Appl. No.: 635,913

[22] Filed: Jul. 30, 1984

[30] Foreign Application Priority Data

Aug. 9, 1983 [JP] Japan ............................ 58-144478

[51] Int. Cl.$^3$ ............................................ G01N 27/58
[52] U.S. Cl. .............................. 204/424; 427/123; 427/126.2; 427/126.3
[58] Field of Search ............ 204/421, 422, 424, 425, 204/426, 427, 428, 429, 15; 427/123, 126.2, 126.3

[56] References Cited

U.S. PATENT DOCUMENTS

| | | | |
|---|---|---|---|
| 3,843,400 | 10/1974 | Radford | 204/421 X |
| 4,170,530 | 10/1979 | Watanabe et al. | 204/426 |
| 4,280,890 | 7/1981 | Friese et al. | 204/421 |
| 4,283,441 | 8/1981 | Haecker et al. | 204/424 X |

*Primary Examiner*—G. L. Kaplan
*Attorney, Agent, or Firm*—Parkhurst & Oliff

[57] ABSTRACT

An electrochemical cell has a layer of sintered mixture, i.e., an electrode, consisting of a platinum group metal and an oxygen-ion-conductive solid electrolyte, whose interstices are stuffed with an oxygen-ion-conductive solid electrolyte heat treated at a temperature below the sintering temperature of the layer of sintered mixture.

The electrochemical cell can be used at low temperature as an oxygen sensor or an oxygen pump. Further an excellent durability is ensured even when the electrochemical cell is used in a high-speed stream of high-temperature gas.

4 Claims, No Drawings

ELECTROCHEMICAL CELL AND METHOD OF PRODUCING THE SAME

BACKGROUND OF THE INVENTION

1. Field of the Invention

The invention relates to an electrochemical cell which operates even at low temperatures and has a high durability.

2. Description of the Prior Art

Heretofore, electrochemical elements have been made by forming a sintered oxygen-ion-conductive solid electrolyte body by using for instance zirconium oxide added with calcia (CaO), yttria ($Y_2O_3$), or the like and mounting electrodes such as platinum electrodes on the oxygen-ion-conductive solid electrolyte body. In fact, such electrochemical elements are electrochemical cells which have been used as oxygen sensors for detecting oxygen partial pressure in boiler exhaust gas and automobile exhaust gas or as oxygen pumping for pumping in oxygen to a gas or pumping out from a gas.

The electrode of the electrochemical cell for such use is required to have a small impedance at the boundary between it and the underlying body of oxygen-ion-conductive solid electrolyte, so as to generate an output electromotive force even at low temperatures. The electrode is also required to have a strong bond with the oxygen-ion-conductive solid electrolyte body, so as to provide a high durability even if it is used in a stream of very hot gas with a high flow rate.

The internal impedance of an electrochemical cell can be treated as the sum of the intrinsic impedance of the solid electrolyte body and the boundary impedance between the electrode and the underlying solid electrolyte body. The intrinsic impedance of the solid electrolyte is determined almost exclusively by the chemical composite thereof, while it is known that the boundary impedance varies over a wide range depending on the manner in which the electrode is attached to the solid electrolyte body. Thus, to produce an electrochemical cell which operates and generates a significant electromotive force at low temperatures, the boundary impedance at the electrode must be minimized.

In general, platinum group metals are used as the electrode of the electrochemical cell for such use, which are provided by chemical plating methods, physical plating methods, baking methods and the like on the surface of the solid electrolyte body. However, the electrode thus provided has a shortcoming in that the bond of the platinum group alloy with the underlying oxygen-ion-conductive solid electrolyte body is a mere mechanical coupling, and the electrode plate tends to float fairly easily from the surface of the solid electrolyte, when exposed to thermal stress or the like, resulting in an increase of the boundary impedance or even exfoliation of electrode in the worst case.

It is also known that an electrode with a low boundary impedance can be formed by applying a film of a platinum group metal on the surface of solid electrolyte by plating or baking, impregnating interstices in the thus applied film with a solution of an oxide forming metal compound, and heating the electrode so as to produce zirconium oxide and the like in the interstices as a decomposition product thereof. The thus formed electrode has a low boundary impedance, but is has a shortcoming in that its bond with the underlying oxygen-ion-conductive solid electrolyte is weak as in the case described above. In short, the boundary impedance is improved but the bonding strength is not improved.

If an improvement of the bonding strength of such electrode is tried by effecting the heating of the metal oxide solution at 1,100° C. or higher while expecting possible reaction or sintering of the metal oxide with the underlying oxygen-ion-conductive solid electrolyte, the boundary impedance increases considerably. Thus, due to the restriction from the standpoint of boundary impedance, there are limits to improvement of the bonding strength of the electrode to the underlying solid electrolyte in this case too.

As an electrode of an electrochemical cell having a high bonding strength, a cermet electrode for the electrochemical cell such as an oxygen concentration cell has been known. The cermet electrode is formed by applying an electrode-forming mixture consisting of powder of a platinum group metal with powder of an oxygen-ion-conductive solid electrolyte on a desired surface of the underlying oxygen-ion-conductive solid electrolyte body, and firing them at a temperature high enough to result in sufficient reaction of the underlying solid electrolyte with the oxygen-ion-conductive electrolyte in the electrode-forming mixture for establishing a firm bond therebetween. However, such a cermet electrode for an oxygen concentration cell and the like has a shortcoming in that it has a high boundary impedance because it is treated at a high temperature sufficient for causing firm bond between the solid electrolyte in the electrode-forming mixture and the underlying oxygen-ion-conductive solid electrolyte body, and hence it does not produce any significant electromotive force at low temperatures.

SUMMARY OF THE INVENTION

Therefore, an object of the present invention is to obviate the above-mentioned shortcomings of the prior art by providing an improved electrochemical cell whose electrode is firmly bonded to the underlying solid electrolyte body so as the render a high durability. The electrode in the electrochemical cell of the invention has a small boundary impedance between it and the underlying solid electrolyte body, so that the electrochemical cell operates satisfactorily even at low temperatures.

To fulfill the above-mentioned object, an electrochemical cell according to the present invention comprises an oxygen-ion-conductive solid electrolyte body, and at least one electrode formed of a layer of sintered mixture consisting of a platinum group metal and an oxygen-ion-conductive solid electrolyte. Preferably, the sintered mixture of the electrode is fired simultaneously with the solid electrolyte body. The electrode is bonded to the electrolyte body and has an oxygen-ion-conductive solid electrolyte stuffed in interstices of the sintered mixture of the electrode, the solid electrolyte in the inerstices being heat treated at a temperature lower than the sintering temperature of the sintered mixture.

In a method of producing an electrochemical cell according to the invention, a layer of sintered mixture is formed on the surface of an oxygen-ion-conductive solid electrolyte body, which mixture consists of a platinum group metal and an oxygen-ion-conductive solid electrolyte. Interstices of the layer of sintered mixture are impregnated with a liquid, which liquid is either a suspension of fine powder particles of an oxygen-ion-conductive solid electrolyte or a solution of a metallic compound capable of generating an oxygen-ion-conductive solid electrolyte upon heating. The thus impregnated layer formed on the solid electrolyte body is heated at a temperature below the sintering temperature of the sintered mixture.

Preferably, in carrying out the above-mentioned method of producing an electrochemical cell according to the invention, the layer of sintered mixture is made by forming a layer of paste on a surface of a shaped body of a metallic compound capable of generating an oxygen-ion-conductive solid electrolyte upon heating, which paste consists of a mixture of a platinum group metal and a metallic compound capable of generating an oxygen-ion-conductive solid electrolyte, and firing the layer of paste thus formed on the shaped body.

The invention is based on the inventor finding that an active electrode, having a low boundary impedance toward its underlying electrolyte body, can be produced by sintering a layer of sintered mixture, consisting of a platinum group metal and an oxygen-ion-conductive solid electrolyte, together with the underlying oxygen-ion-conductive solid electrolyte body at a temperature suitable for producing the strongest bond between the mixture and the solid electrolyte body, and impregnating interstices in the thus sintered layer of sintered mixture, i.e., an electrode, with an oxygen-ion-conductive solid electrolyte heat treated at a temperature below the sintering temperature of the sintered mixture, preferably below 1,100° C. It has been noted that the sintering of the electrode together with the underlying solid electrolyte body at the above-mentioned temperature tends to reduce the activity of the electrode and increase the boundary impedance of the electrode, but the above-mentioned impregnation re-activates the electrode and reduces the boundary impedance of the electrode once again.

In determining the chemical composition of the electrode made of the sintered mixture of a platinum group metal and an oxygen-ion-conductive solid electrolyte, it is noted that the smaller the reduction of its activity at the sintering is, the easier the above re-activation will be. Thus, the alleviate the excessive activity reduction of the platinum group metal at sintering, it is preferable that the electrode contains more than 25 parts by volume of an oxygen-ion-conductive solid electrolyte for 100 parts by volume of a platinum group metal, while this content of the oxygen-ion-conductive solid electrolyte is preferably less than 200 parts by volume to ensure proper electric conductivity of the electrode.

Examples of the oxygen-ion-conductive solid electrolyte to be used in the present invention are zirconia ($ZrO_2$) or hafnium oxide ($HfO_2$) added with yttria ($Y_2O_3$), calcia (CaO), magnesia (MgO), ytterbium oxide ($Yb_2O_3$), scandium oxide ($Sc_2O_3$), neodymium oxide ($Nd_2O_3$), cerium oxide ($CeO_2$), and the like; cerium oxide ($CeO_2$) added with lanthanum oxide ($La_2O_3$), yttria ($Y_2O_3$), neodymium oxide ($Nd_2O_3$), thorium oxide ($ThO_2$), and the like; and thorium oxide ($ThO_2$) added with calcia (CaO), yttria ($Y_2O_3$), lanthanum oxide ($La_2O_3$), and the like.

The layer of sintered mixture consisting of a platinum group metal and an oxygen-ion-conductive solid electrolyte may be formed as follows; namely, a mixture of powder of a platinum group metal such as platinum and powder of an oxygen-ion-conductive solid electrolyte such as zirconia added with yttria is prepared, for instance in the form of paste, and the mixture is applied to a predetermined surface portion of an oxygen-ion-conductive solid electrolyte body or a shaped body of a metallic compound capable of producing an oxygen-ion-conductive solid electrolyte upon firing, and then the thus applied mixture is fired at a temperature above the sintering temperature of the oxygen-ion-conductive solid electrolyte, preferably above 1,300° C.

To form adequate interstices in the layer of sintered mixture, a suitable amount of additive which evaporates upon firing, such as an organic binder, may be added in the mixture of the platinum group metal powder and the oxygen-ion-conductive solid electrolyte powder.

Examples of the oxygen-ion-conductive solid electrolyte to be stuffed in the interstices of the layer of sintered mixture are zirconia ($ZrO_2$), zirconia added with yttria ($Y_2O_3$), zirconia added with calcia (CaO), zirconia added with ytterbium oxide ($Yb_2O_3$), cerium oxide ($CeO_2$) added with ytterbium oxide, cerium oxide added with yttria ($Y_2O_3$), cerium oxide added with lanthanum oxide ($La_2O_3$), thorium oxide ($ThO_2$) added with yttria, thorium oxide added with calcia, and the like, or a mixture of two or more of the foregoing solid electrolytes.

An electrode made of the layer of sintered mixture having interstices stuffed with the above oxygen-ion-conductive solid electrolyte heat treated at a temperature below the sintering temperature of the sintered mixture can be produced in the following manner; namely, a suspension is prepared by dispersing fine powder particles of one or more of the above oxygen-ion-conductive solid electrolytes in a suitable solvent such as water, alcohol, or the like, and the suspension is applied to the sintered mixture either by brushing or by dipping the sintered mixture in the suspension, and then the sintered mixture with the suspension thus applied thereto is dried and heat treated at a temperature below the sintering temperature of the sintered mixture, preferably below 1,100° C.

Instead of the above suspension, a solution of one or more of metallic compounds capable of generating the desired oxygen-ion-conductive solid electrolyte upon heating such as zirconium oxychloride, yttrium chloride, and the like may be used. To reduce the boundary impedance between the electrode and the underlying oxygen-ion-conductive solid electrolyte body, it is preferable to repeat the above stuffing process several times. In the process of stuffing the interstices of the sintered mixture of the electrode, the oxygen-ion-conductive solid electrolyte for the stuffing may be, of course, deposited on the surfaces of the sintered mixture.

The above process produces an electrochemical cell with an electrode made of a sintered mixture of a platinum group metal and an oxygen-ion-conductive solid electrolyte, the sintered mixture of the electrode having interstices thereof stuffed with an oxygen-ion-conductive solid electrolyte heat treated at a temperature below the sintering temperature of the sintered mixture. The reason why the boundary impedance between the thus formed electrode and the underlying oxygen-ion-conductive solid electrolyte body in the thus produced electrochemical cell is small is probably as follows:

Namely, when the mixture of a platinum group metal and an oxygen-ion-conductive solid electrolyte is strongly bonded to the underlying body by the firing at a temperature above 1,300° C., with the progress of the sintering of the platinum group metal, gaps are formed between the platinum group metal and the oxygen-ion-conductive solid electrolyte in either the sintered mixture or the underlying solid electrolyte body, and the boundary impedance increases once. However, the stuffing of the oxygen-ion-conductive solid electrolyte such as the above zirconia compound heat treated at a temperature below the sintering temperature of the sintered mixture in the interstices of the sintered mixture and other gaps causes formation of a large number of contact points between the platinum group metal and the oxygen-ion-conductive solid electrolyte, and the presence of the large number of contact points thus formed reduces the once increased boundary impedance.

DESCRIPTION OF THE PREFERRED EMBODIMENTS

The invention will be described in further detail now by referring to examples.

EXAMPLE 1

One hundred parts by weight of powder material consisting of 94 mol% of zirconia ($ZrO_2$) and 6 mol% of yttria ($Y_2O_3$) was prepared, and 0.5 part by weight of aluminum oxide was added in the powder material, whereby 502.5 g of starting mixture material was prepared. The mixture material was placed in a polyethylene pot together with zirconia balls, and the material was pulverized and mixed for 48 hours.

A part of the thus pulverized powder material was granulated while adding 5 wt%, based on the amount of the powder material, of 6 wt% aqueous solution of polyvinyl alcohol. The granulated material was shaped by pressing and fired at 1,400° C. for 5 hours, and a disk of an oxygen-ion-conductive solid electrolyte with a diameter of 25.0 mm and a thickness of 0.40 mm was made.

A paste consisting of a platinum group metal and an oxygen-ion-conductive solid electrolyte for the layer of sintered mixture was prepared by mixing 2.14 g of platinum powder, 0.55 g of the above powder material which was pulverized for 48 hours, 0.135 g of ethylcellulose as a binder, a butyl carbitol acetate as an organic solvent, and agitating the mixture in an agate mortor for 30 minutes. The paste was applied to opposite surfaces of the above disk of the oxygen-ion-conductive solid electrolyte by brushing, and after being dried at 80° C. for 30 minutes, the disk with the paste was fired at 1,450° C. for one hour. The fired disk was found to have layers of sintered mixture firmly bonded to the disk body.

A liquid containing zirconia oxide was prepared by dispersing 10 g of fine powder particles of zirconium oxide in 10 ml of ethyl alcohol. A Specimen 1 of the electrochemical cell of the invention was made by impregnating the interstices of the sintered mixture of the above fired disk with the liquid thus prepared by dipping it in the above liquid for one minute, drying the disk removed from the liquid, and heating the thus impregnated disk at 1,050° C. for ten minutes.

The DC electric resistance of the Specimen 1 at 350° C. and 450° C. was measured by placing it in an electric furnace. During the measurement, Specimen 1 was held securely by keeping it on a platinum sheet having a platinum lead wire extending to the outside of the furnace, covering its top with another platinum sheet with a platinum lead wire extending to the outside of the furnace, and laying a stainless steel weight on the top surface of the covering platinum sheet.

The result of the measurement of the DC resistance is shown in Table 1.

EXAMPLE 2

The same disk of the oxygen-ion-conductive solid electrolyte with the layers of sintered mixture as that of Example 1 was made. An aqueous solution was prepared by dissolving 100 g of zirconium oxychloride in 150 ml of water.

A Specimen 2 of the electrochemical cell of the invention was made by impregnating the interstices of the sintered mixture of the above fired disk with the aqueous solution thus prepared by dipping it in the above aqueous solution, and heating the thus impregnated disk at 1,050° C. for ten minutes.

The DC electric resistance of the Specimen 2 at 350° C. and 450° C. was measured in the same manner as that of Example 1.

The result of the measurement of the DC resistance is shown in Table 1.

EXAMPLE 3

A Specimen 3 of the electrochemical cell of the invention was prepared by making the same disk as that of the Example 2, and subjecting the disk to four times of the same impregnation followed by the same heating at 1,050° C. for ten minutes as those of Example 2.

The DC electric resistance of the Specimen 3 at 350° C. and 450° C. was measured in the same manner as that of Example 1.

The result of the measurement of the DC resistance is shown in Table 1.

EXAMPLE 4

The same disk of the oxygen-ion-conductive solid electrolyte with the layers of sintered mixture as that of Example 1 was made.

A liquid was prepared by dispersing 10 g of fine powder particles of oxygen-ion-conductive solid electrolyte consisting of 94 mol% of zirconia ($ZrO_2$) and 6 mol% of yttria ($Y_2O_3$) in 10 ml of ethyl alcohol.

A Specimen 4 of the electrochemical cell of the invention was made by impregnating the interstices of the sintered mixture of the above fired disk with the liquid thus prepared by dipping it in the above liquid for one minute, drying the disk after removing from the liquid, heating the thus impregnated disk at 1,100° C. for ten minutes, and repeating the above dipping, drying and firing once again.

The DC electric resistance of the Specimen 4 at 350° C. and 450° C. was measured in the same manner as that of Example 1.

The result of the measurement of the DC resistance is shown in Table 1.

EXAMPLE 5

The same disk of the oxygen-ion-conductive solid electrolyte with the layers of sintered mixture as that of Example 1 was made.

An aqueous solution was prepared by dissolving 100 g of zirconium oxychloride and 12.02 g of yttrium chloride with six times of water of crystallization in 150 ml of water.

A specimen 5 of the electrochemical cell of the invention was made by impregnating the interstices of the sintered mixture of the above fired disk with the aqueous solution thus prepared by dipping it in the above aqueous solution, drying the disk after removing it from the aqueous solution, heating the thus impregnated disk at 1,000° C. for ten minutes, and repeating the above dipping, drying and firing once again.

The DC electric resitance of the Specimen 5 at 350° C. and 450° C. was measured in the same manner as that of Example 1.

The result of the measurement of the DC resistance is shown in Table 1.

EXAMPLE 6

The granulated material prepared in Example 1 by adding polyvinyl alcohol in the powder mixture pulverized for 48 hours was shaped into a disk by pressing. Before firing, the paste prepared in Example 1 for the layer of sintered mixture was applied to opposite surfaces of the thus shaped disk by brushing. Then, the disk with the paste layers was fired at 1,425° C. for 3 hours, and a disk of an oxygen-ion-conductive solid electrolyte having layers of the sintered mixture was made.

the aqueous solution, heating the thus impregnated disk at 1,000° C. for ten minutes, and repeating three more times the above dipping, drying and firing.

The DC electric resistance of the Specimen 7 at 350° C. and 450° C. was measured in the same manner as that of Example 1.

The result of the measurement of the DC resistance is shown in Table 1.

For comparison, a Reference Specimen 8 was prepared by making the disk having the layer of sintered mixture consisting of platinum and the oxygen-ion-conductive solid electrolyte in the same manner as Example 1 but without applying the succeeding impregnation of the oxygen-ion-conductive solid electrolyte in the interstices of the above layer. The DC electric resistance of Reference Specimen 8 was also measured at 350° C. and 450° C., and the result of the measurement is also shown in Table 1.

TABLE 1

| Invention, Reference | Sample No. | Making of sintered mixture layer* | Impregnation** Method | Number of repeat | DC resistance*** (KΩ) at 350° C. | at 450° C. | Remarks |
|---|---|---|---|---|---|---|---|
| Invention | 1 | Note 1 | Note 3 | 1 | 50.0 | 4.17 | Layer of sintered |
|  | 2 | " | Note 4 | 1 | 35.9 | 2.09 | mixture was bonded |
|  | 3 | " | " | 4 | 19.5 | 1.10 | very strongly. |
|  | 4 | " | Note 5 | 2 | 43.3 | 3.43 |  |
|  | 5 | " | Note 6 | 2 | 35.5 | 2.01 |  |
|  | 6 | Note 2 | " | 2 | 31.0 | 1.87 |  |
|  | 7 | " | Note 7 | 4 | 36.9 | 2.03 |  |
| Reference | 8 | Note 1 | None | 0 | 91.4 | 11.4 |  |

NOTES:
*Method of making a layer of sintered mixture consisting of platinum and oxygen-ion-conductive solid electrolyte.
**Method of impregnating the above layer of sintered mixture with an oxygen-ion-conductive electrolyte.
***Average resistance of six samples.
[1] A disk consisting 100 parts by weight of a powder mixture containing 94 mol % $ZrO_2$ and 6 mol % $Y_2O_3$ and 0.5 part by weight of $Al_2O_3$ was fired at 1,400° C., and paste consisting of the above powder mixture and platinum powder was brushed on opposite surfaces of the disk, and fired at 1,450° C.
[2] Before firing the above disk, the above paste containing platinum powder was brushed on the disk, and the disk and paste were fired together at 1,425° C.
[3] Dipped in alcohol solution of $ZrO_2$ fine powder particles, and heat treated at 1,050° C. for 10 minutes.
[4] Dipped in aqueous solution of $ZrOCl_2$, and heat treated at 1,050° C. for 10 minutes.
[5] Dipped in alcohol solution of $ZrO_2$—$Y_2O_3$ fine powder particles, and heat treated at 1,100° C.
[6] Dipped in aqueous solution of $ZrOCl_2$—$YCl_3$, and heat treated at 1,000° C. for 10 minutes.
[7] Dipped in aqueous solution of $ThCl_4$—$YCl_3$, and heat treated at 1,000° C. for 10 minutes.

A Specimen 6 of the electrochemical cell of the invention was made by impregnating the interstices of the sintered mixture of the above fired disk with the aqueous solution of zirconium oxychloride and yttrium chloride prepared in Example 5 by dipping it in the above aqueous solution, drying the disk after removing it from the aqueous solution, heating the thus impregnated disk at 1,000° C. for ten minutes, and repeating the above dipping, drying and firing once again.

The DC resistance of the Specimen 6 at 350° C. and 450° C. was measured in the same manner as that of Example 1.

The result of the measurement of the DC resistance is shown in Table 1.

EXAMPLE 7

The same disk of the oxygen-ion-conductive solid electrolyte with the layers of sintered mixture as that of Example 6 was made.

An aqueous solution was prepared by dissolving 100 g of thorium chloride and 28.64 g of yttrium chloride with water of crystallization in 100 ml of water.

A Specimen 7 of the electrochemical cell of the invention was made by impregnating the interstices of the sintered mixture of the above fired disk with the aqueous solution thus prepared by dipping it in the above aqueous solution, drying the disk after removing it from As shown in Table 1, the electrochemical cell according to the present invention has a small DC resistance across the cell, so that it can be advantageously used even at low temperatures as a sensor to detect oxygen partial pressure or as an oxygen pump. Having a very strong bond between the underlying solid electrolyte body and the layer of sintered mixture consisting of a platinum group metal and an oxygen-ion-conductive solid electrolyte, the electrochemical cell of the invention has an outstandingly high durability when used in a high-speed stream of high-temperature gas. The electrochemical cell without any stuffing of the invention has a very high DC resistance and inferior low-temperature performance to that of the invention, as proven by Reference Specimen 8.

As described in detail in the foregoing, an electrochemical cell according to the present invention has a layer of sintered mixture, i.e., an electrode, consisting of a platinum group metal and an oxygen-ion-conductive solid electrolyte, whose interstices are stuffed with an oxygen-ion-conductive solid electrolyte heat treated at a temperature below the sintering temperature of the layer of sintered mixture. Thus, the electrochemical cell can be used even at low temperatures as a sensor for measuring oxygen partial pressure in a gas or as an oxygen pump. Further, since the electrode in the electrochemical cell of the invention has a very strong bond to the underlying solid electrolyte body, an excellent durability is ensured even when the electrochemical cell is used in a high-speed stream of high-temperature gas. The electrochemical cell is very useful as an oxygen sensor or as an oxygen pump to be used in high-temperature exhaust gas from an automobile engine or a boiler, so that the invention contributes greatly to the industry.

Although the invention has been described with a certain degree of particularity, it is to be understood that the present disclosure has been made only by way of example and that numerous changes in details of construction and the combination and arrangement of parts may be resorted to without departing from the scope of the invention as hereinafter claimed.

What is claimed is:

1. An electrochemical cell, comprising an oxygen-ion-conductive solid electrolyte body, and at least one electrode formed of a layer of sintered mixture consisting of a platinum group metal and an oxygen-ion-conductive solid electrolyte, said electrode being bonded to said solid electrolyte body and having an oxygen-ion-conductive solid electrolyte stuffed into interstices of said sintered mixture of the electrode, said solid electrolyte in said interstices being heat treated at a temperature lower than sintering temperature of said sintered mixture.

2. An electrochemical cell as set forth in claim 1, wherein said cell is made of a simultaneously fired assembly of said oxygen-ion-conductive solid electrolyte body and said electrode formed of a layer of sintered mixture consisting of a platinum group metal and an oxygen-ion-conductive solid electrolyte.

3. A method of producing an electrochemical cell, comprising steps of forming a layer of sintered mixture on a surface of an oxygen-ion-conductive solid electrolyte body, said mixture consisting of a platinum group metal and an oxygen-ion-conductive solid electrolyte, impregnating interstices of said layer of sintered mixture with a liquid selected from the group consisting of a suspension of fine powder particles of an oxygen-ion-conductive solid electrolyte and a solution of metallic compound capable of generating an oxygen-ion-conductive solid electrolyte upon heating, and heating the thus impregnated layer formed on said solid electrolyte body at a temperature below sintering temperature of said layer of sintered mixture.

4. A method of producing an electrochemical cell as set forth in claim 3, wherein said layer of sintered mixture is made by forming a layer of paste on a surface of a shaped body of a metallic compound capable of generating an oxygen-ion-conductive solid electrolyte upon heating, said paste consisting of a mixture of a platinum group metal and a metallic compound capable of generating an oxygen-ion-conductive solid electrolyte upon heating, and firing simultaneously said layer of paste thus formed on said shaped body.

* * * * *